United States Patent [19]

Gould et al.

[11] 4,424,305

[45] Jan. 3, 1984

[54] SURGICAL IMPLANTS FORMED OF POLYURETHANE DIACRYLATE COMPOSITIONS

[75] Inventors: Francis E. Gould, Princeton; Christian W. Johnston, Neshanic Station, both of N.J.

[73] Assignee: Tyndale Plains-Hunter, Ltd., Princeton, N.J.

[21] Appl. No.: 413,942

[22] Filed: Sep. 1, 1982

Related U.S. Application Data

[62] Division of Ser. No. 206,407, Nov. 12, 1980, Pat. No. 4,359,558.

[51] Int. Cl.³ .................. C08F 8/30; C08G 18/10; C08G 18/14; A61K 31/74
[52] U.S. Cl. ............................. 525/127; 454/78; 454/167; 521/905; 525/454; 525/455; 528/75; 528/904
[58] Field of Search ............... 525/127, 454, 455; 528/75, 904; 521/905; 424/78, 167

[56] References Cited

U.S. PATENT DOCUMENTS

| 3,297,745 | 1/1967 | Fekete et al. | 525/920 |
| 3,931,123 | 1/1976 | Vacik et al. | 526/320 |
| 3,940,542 | 2/1976 | Knopf et al. | 428/364 |
| 3,975,350 | 8/1976 | Hudgin et al. | 521/905 |
| 4,056,496 | 11/1977 | Mancini et al. | 523/106 |
| 4,116,786 | 9/1978 | Hodakowski | 204/159.13 |
| 4,117,184 | 9/1978 | Erickson et al. | 428/224 |
| 4,156,066 | 5/1979 | Gould | 424/32 |
| 4,156,067 | 5/1979 | Gould | 424/32 |
| 4,250,248 | 2/1981 | Faust | 525/127 |
| 4,255,550 | 3/1981 | Gould | 528/44 |

*Primary Examiner*—H. S. Cockeram
*Attorney, Agent, or Firm*—Robert W. Kell; George F. Mueller

[57] ABSTRACT

Surgical implants, intrauterine devices and the like formed of polyurethane diacrylate compositions obtained by reacting a diacrylate in the presence of from about 65 to about 95 weight percent of a hydrophilic polyurethane resin. The compositions will form a hydrogel upon immersion in water and are permeable to gases, ions and other low molecular weight species. The hydrophilic polyurethane diacrylate compositions may be molded to form shaped products that are dimensionally stable after repeated exposure to boiling water and exhibit memory. The shaped products contain distributed therein a desired medicament.

19 Claims, No Drawings

SURGICAL IMPLANTS FORMED OF POLYURETHANE DIACRYLATE COMPOSITIONS

This application is a division of application Ser. No. 206,407, filed Nov. 12, 1980, now U.S. Pat. No. 4,359,558.

This invention relates to hydrophilic polyurethane diacrylate compositions. More particularly, the present invention relates to compositions obtained by the reaction of one or more diacrylates in the presence of one or more hydrophilic polyurethanes that may be obtained by the reaction of a polyalkylene glycol with a diisocyanate.

The hydrophilic polyurethane diacrylate compositions of the present invention, will form a hydrogel upon immersion in water, are permeable to gases, ions and other low molecular weight species, are dimensionally stable, even in the presence of boiling water, and exhibit memory.

The hydrophilic polyurethane diacrylate compositions of the present invention may be prepared by reacting a diacrylate in the presence of a hydrophilic polyurethane. A free radical catalyst may be present to initiate the reaction of the diacrylate.

The hydrophilic polyurethanes that are employed as one component of the present compositions may be made by the reaction of:
(A) one or more diols having a number average molecular weight in the range of from about 200 to 20,000, selected from the group consisting of:
  (a) diethylene glycol, and
  (b) long chain polyoxyalkylene diols, with
(B) a urethane precursor selected from the group consisting of organic polyisocyanates and nitrile carbonates in the presence of an organic tin catalyst. If desired, a polyfunctional lactone having the formula:

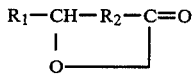

wherein $R_1$ is a monovalent radical selected from the group consisting of —H, —CH$_2$NH$_2$, —SO$_2$CH$_3$, —CHOHCOOH, and —(CHOH)$_n$CH$_2$OH; n being an integer from 0 to 5; and $R_2$ is a divalent radical —(—CHOH)$_m$—; m being an integer from 2 to 10; and ethers derived from said lactones; may be added in amounts of from 0.1% to 30% of the weight of the total reaction mixture. Polyurethane resins containing such polyfunctional lactones are described in U.S. Pat. Nos. 4,156,066, 4,156,067 and 4,255,550.

The hydrophilic polyurethane component which is present with the diacrylate at the time of its reaction contains diethylene glycol and a long-chain water soluble diol. The long-chain, water-soluble diols should have a molecular weight of at least about 200 and preferably 1450 to 7500 and may be derived from ethers, i.e., ethylene oxide and propylene oxide. Suitable diols consist predominantly of oxyethylene or oxypropylene groups, though a minor proportion of other oxyalkylene groups may be included.

The polyisocyanate used to make the first component of the present compositions may be represented by R(NCO)$_n$ wherein n is greater than 1, preferably 2–4, and R is an aliphatic, alicyclic, aliphatic-alicyclic, aromatic, or aliphatic-aromatic hydrocarbon compound of from 4 to 26 carbon atoms, but more conventionally from 6 to 20 and generally from 6 to 13 carbon atoms. Representative examples of the above isocyanates are: tetramethylene diisocyanate; hexamethylene diisocyanate; trimethylhexamethylene diisocyanate; dimer acid diisocyanate; isophorone diisocyanate; diethylbenzene diisocyanate; decamethylene 1,10-diisocyanate; cyclohexylene 1,2-diisocyanate and cyclohexylene 1,4-diisocyanate and the aromatic isocyanates such as 2,4- and 2,6-tolylene diisocyanate; 4,4-diphenylmethane diisocyanate; 1,5-naphthalene diisocyanate; dianisidine diisocyanate; tolidine diisocyanate; a polymeric polyisocyanate such as neopentyl tetra isocyanate; m-xylylene diisocyanate; tetrahydronaphthalene-1,5 diisocyanate; and bis(4-isocyanatophenyl) methane.

The preferred isocyanate is methylene di(cyclohexyl isocyanate). Other but slightly less preferred diisocyanates are trimethyl hexamethylene diisocyanate and isophorone diisocyanate.

Other compounds which are useful are the isocyanate equivalents which produce the urethane linkages such as the nitrile carbonate, i.e., the adiponitrile carbonate of the formula:

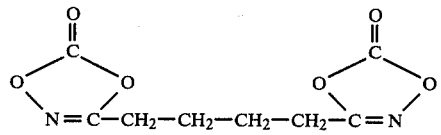

In the manufacture of the hydrophilic polyurethane resin component of this invention, low molecular weight glycols such as diethylene glycol and dipropylene glycol or an aromatic glycol may be added to the reaction mixture. The preferred low molecular weight aromatic polyols are bisphenol A and 4,4'-sulfonyldiphenol.

The proportions in which the long chain polyglycol and the low molecular weight glycol, i.e, diethylene glycol are present in the hydrophilic polyurethane component of this invention depends on the hydrophobic-hydrophilic balance present in each and desired in the final composition. Increasing the molecular weight of the long-chain polyoxyethylene glycol and/or the amount of this polyol contributes strong hydrophilic properties to the final product. This effect may be counter-balanced by increasing the proportion of low molecular weight glycol, i.e., diethylene glycol or dipropylene glycol.

Keeping the above in mind (that it is the number of polyethylene oxide groups in the polymer molecular that determines hydrophilic properties and the polyethylene oxide groups are more hydrophilic than are polypropylene oxide groups) it is a simple matter to choose mixtures of reactants such that the hydrophilic polyurethane to be present at the time of reacting the diacrylate will have the desired properties. By choosing the molecular weight of the polyethylene glycol or using two polyalkylene glycols of different molecular weight one may "tailor make" the hydrophilic polyurethane component to satisfy a wide range of properties. It will be understood that the term "hydrophilic polyurethanes" as used throughout the specification and claims is used to describe polyurethanes which form hydrogels through hydrogen bonding and which take up at least 20 weight percent water then immersed in water. More-over, the hydrophilic polyurethane diacrylate compositions of the present invention, like the hydrophilic polyurethane component also form hydrogels when immersed in water that take up at least 20 weight percent water.

As mentioned above, the hydrophilic polyurethane component that is reacted with diacrylate to form the compositions of the present invention may contain a polyfunctional lactone. Representative examples of the polyfunctional lactones are those derived from polysaccharides and monosaccharides such as mannolactone, delta gluconolactone, sorbolactone and D-glucuronolactone.

It is desirable that the lactones employed have at least 3 and preferably 4 or more hydroxyl groups in the molecule or at least 1 more than is required to form a linear polyurethane chain. These free (unreacted) hydroxyl groups remain in the polymer backbone and are available for crosslinking the polymer. The lactone ring is also reactive and may be opened, i.e., by hydrolysis, to form carboxylate groups or carboxyl groups in the polymer backbone.

In making the first component of the present invention, the glycols are mixed with the lactone, if present, and the polyisocyanate is reacted with the mixture although other techniques may be used. The reaction is catalyzed by known catalyst for such reaction, suitable ones being tin salts and organic tin esters such as dibutyl tin dilaurate, tertiary amines such as triethyl diamine (DABCD), N,N,N',N'-tetramethyl-1,3-butane diamine and other recognized catalyst for urethane reactions which are well known in the art. The reaction can be conducted in the absence or presence of diluent or solvent.

The second component of the composition of the present invention is a diacrylate which may be obtained by reacting acrylic acid chloride (propenoyl chloride) or methacrylic acid chloride (2-methyl propenoyl chloride) with a glycol. The preferred diacrylate is diethylene glycol diacrylate although the diacrylate of ethylene glycol and polyethylene glycols having a number average molecular weight between 62 and about 1,450 may also be used.

In preparing the hydrophilic polyurethane diacrylate composition of the present invention, the one or more polyurethanes are preferably dissolved together with one or more diacrylates in a solvent such as methanol or 95% ethanol and a free radical catalyst is added to initiate polymerization of the diacrylate. The solution of the two components may be cast to form a film and heat cured at temperatures in the range of 110° C. to 135° C. or alternatively, the cast film may be cured by the action of ultraviolet light. If insolubilization of the two component composition is to be initiated by ultraviolet light, it is not necessary that the free radical catalyst be present. It may be desirable, however, to add an ultraviolet absorber such as Rhodamine B or an azo type catalyst such as azo bis-isobutyryl nitrile to the mixture of the two components.

If it is desired to prepare shaped articles or tubing from the hydrophilic polyurethane diacrylate compositions of the present invention, the solvent may be removed under reduced pressure and the residual mixture can be molded at temperatures of 110° C. to 135° C. for from about 2 to about 20 minutes to cure and insolubilize the hydrophilic polyurethane diacrylate composition.

The polyurethane diacrylate compositions of the present invention may also be prepared "in situ" by reacting a mixture of the monomers that form the polyurethane in the presence of a diacrylate, an organic tin catalyst and a free radical catalyst. The resulting two component mixtures will further react upon heating or exposure to ultraviolet light.

The hydrophilic polyurethane diacrylate compositions of the present invention are dimensionally stable upon repeated exposure to boiling water and have unique physical properties that are of advantage when used in the manufacture of soft contact lens.

The above described hydrophilic polyurethane diacrylate resin compositions are also useful as coatings, molding compounds, absorbents, controlled release agents, ion exchange resins, and in the manufacture of dialysis membranes, dentures, cannulae, contact lenses, packaging components, burn dressings, contraceptive devices, sutures, surgical implants, blood oxygenators, intrauterine devices, vascular prostheses, oral delivery systems, battery separator plates, eye bandages, corneal prostheses, antifog coatings, surgical drapes, oxygen exchange membranes, artificial finger nails, finger cots, adhesives, gas permeable membranes, and in protective and drag resistant coatings.

The practice of the invention is further illustrated by the following examples without being restricted thereto, the parts being by weight, unless otherwise stated.

EXAMPLE I

A polyurethane polymer is prepared by melting together in a container 822.3 parts of CARBOWAX 6000 ® (a polyethylene glycol having a number average molecular weight of 7,500 manufactured by Union Carbide Corporation, New York, N.Y. 10017), 23.0 parts of diethylene glycol, 5.4 parts of water and 149.7 parts of methylene bis-cyclohexyl-4,4'-isocyanate (a product identified as DESMODUR W ® by the Mobary Chemical Corporation, Penn Lincoln Parkway West, Pittsburgh, Pa. 15205). The mixture is stirred at 75° C. for 15 minutes until homogeneous, cooled to 50° C. and then there is added 2.0 parts by volume of an organic tin catalyst solution, dibutyl tin dilaurate (a product identified as $T_{12}$ (manufactured by Metal and Thermite Company of Rahway, N.J.). The catalyst is added and the reaction mixture is allowed to exotherm from 50° C. to 75° C. The molten product is poured at a temperature of 75° C. into Teflon coated polypropylene pans and heated in an oven at 100° C. to complete the reaction and form a solid hydrophilic polyurethane product.

The polyurethane product is cooled to room temperature, removed from the pans and dissolved in 95% ethanol to give a solution containing 10 percent by weight solids. To 4000 parts of this polyurethane solution in ethanol is added with stirring 100 parts of diethylene glycol diacrylate and 0.208 parts by volume of isobutyl peroxy octoate. The solvent is evaporated at room temperature under vacuum to give a product that is subsequently molded in the shape of a contact lens at 125° C. for 30 minutes. The product is dimensionally stable and may be repeatedly boiled in water and cooled to room temperature without any perceptible change in its shape. This product exhibits elastic memory as it may be compressed into a flat sheet in a press at elevated temperatures and permitted to cool. When placed in water, the flat sheet will revert to its original lens shape.

In a similar manner, lenses may be prepared from the polyurethane of this Example by reacting in the presence of 10–30 weight percent diethylene glycol diacrylate.

EXAMPLE II

A polyurethane resin is prepared as described above in Example I by melting together:
Polyethylene glycol (m. wt. 1450): 1232 parts
Diethylene glycol: 134 parts
Water: 6 parts
DESMODUR W ®: 628 parts Three parts by volume of a stannous octoate catalyst identified as T$_9$ by the Metal and Thermite Company of Rahway, N.J. is added to the reaction mixture at a temperature of 50° C. The temperature initially rises at a slow rate and then more rapidly. When the temperature reaches 85° C., the reaction mass is poured into Teflon coated pans, placed in an oven with forced air circulation at 100° C. for 30 minutes and then cooled to room temperature.

The formed polyurethane is dissolved in 18,000 parts of 95% ethanol and 222 parts of diethylene glycol diacrylate and 0.44 parts of tertiary-butyl-peroctoate and added with thorough mixing. The solvent is removed at room temperature to produce a white plastic mass that is somewhat sticky when first prepared.

The plastic mass is placed in a mold and molded at 135° C. for 20 minutes to give a cured (crosslinked) hydrophilic polymer having application in the manufacture of soft contact lens. When immersed in water, the molded product will absorb sufficient water to increase in weight 200 percent.

If desired, the polyurethane-diethylene glycol diacryllate composition described above in this Example may be mixed with, or used to encapsulate drugs prior to the curing step. The cured polymer will slowly release the drug when placed in an aqueous or saline solution or in body fluids. The resin composition described in this Example, therefore, may be formed into any convenient shape, i.e., tablets for oral ingestion, implants, and suppositories to provide a controlled release of the drug.

EXAMPLE III

A hydroxyl terminated polyurethane resin is prepared by the method described in Example II above from the following reaction mixture:
Polyethylene glycol (m. wt. 1450): 977 parts
Diethylene glycol: 211 parts
DESMODUR W ®: 807 parts
Stannous octoate: 1.3 parts The polyurethane polymer is modified with 25 weight percent diethylene glycol diacrylate as described above in Example II using:
Diethylene glycol diacrylate: 667 parts
Tertiary-butyl-perbenzoate 1.3 parts The polyurethane-diacrylate composition is more rigid than that prepared in Example II above. It is pressed into the form of a flat sheet by heating under pressure in a press at 100° C. and increasing the temperature to 130° C. for 2 minutes while maintaining the pressure. The sheet may be used as a membrane for water and vapor transmissions and has medicinal applications as permeable dressings, etc. It is particularly advantageous as a burn dressing into which medicaments may be incorporated. The polyurethane-diacrylate composition (containing as little as 5 weight percent diethylene glycol diacrylate) is useful as a dialysis membrane and finds application in separation techniques.

EXAMPLE IV

A polyurethane resin is made by the method described in Example II above from the following reaction mixture:
Polyethylene glycol (m. wt. 7500): 1644 parts
Diethylene glycol: 46 parts
Water: 10 parts
DESMODUR W ®: 300 parts
Dibutyl tin dilaurate: 3 parts The temperature of the reaction mixture increases to 85° C. at which time the mixture is poured into 11 cm×24 cm Teflon coated baking tins and heated in an oven for 1 hour at 100° C.

The polyurethane polymer is cooled to room temperature and modified with 35 percent by weight diethylene glycol dimethacrylate by adding (in ethanol solution) 1077 parts of diethylene glycol dimethacrylate and 2.2 parts of tertiary-butyl-peroctoate.

The polyurethane-diethylene glycol dimethacrylate composition shows a 300 percent increase in weight after being immersed in water for two hours and is a suitable material for molding into a soft contact len. The crosslinked nature of the product permits it to swell in water to an equilibrium value which is not changed by boiling in water for 20 minutes and cooling to room temperature. The boiling and cooling cycle may be repeated many times. Cast or molded films that are useful as wound dressings and will slowly release iodine may be prepared from the resin composition of this Example by incorporating in the polyurethane-diethylene diacryllate composition iodine.

EXAMPLE V

A polyurethane-diethylene glycol diacrylate composition is manufactured "in situ" from the following reaction mixture:
Polyethylene glycol (m. wt. 1450): 1103 parts
Diethylene glycol: 176 parts
Water: 5 parts
Diethylene glycol diacrylate: 500 parts
DESMODUR W ®: 716 parts
n-Butyl-4,4'-bis(t-butylperoxy) valerate: 3.2 parts
Dimethyl ether of hydroquinone: 0.22 parts
Stannous octoate: 2.5 parts The polyethylene glycol, diethylene glycol are melted and mixed together at a temperature below 75° C. and the mixture then cooled to a temperature only slightly above the solidification temperature (50° C.). The hydroquinone is dissolved in the water and added to the glycol mixture with stirring. After the dimethyl ether of hydroquinone is dissolved, the diethylene glycol diacrylate is added with stirring followed by addition of the n-butyl-4,4'-bis(t-butylperoxy) valerate and stannous octoate. The temperature is raised to 60° C. and the DESMODUR W ® is added in small increments. After each addition, there is an exotherm and the temperature is allowed to fall to the extent that the temperature of the reaction mixture may reach 80° C. but never exceeds 85° C.

After all of the DESMODUR W ® has been added, the reaction mixture is allowed to cool to 50° C. and placed in an oven at 50° C. overnight (18 hours). The product is somewhat sticky when first made but this stickiness is reduced upon aging.

EXAMPLE VI

By the procedure described in Example V above, a polyurethane-diethylene glycol dimethacrylate composition is prepared by reacting together:
Polyethylene glycol (m. wt. 1450): 666 parts
Diethylene glycol: 309 parts
Water: 3 parts
Diethylene glycol dimethacrylate: 353 parts
DESMODUR W ®: 1022 parts
Dimethyl ether of hydroquinone: 0.2 parts
Stannous octoate: 0.2 parts The reaction is completed as described in Example V by placing in a forced air circulation oven at 50° C. overnight.

EXAMPLE VII

One thousand parts (2.5 moles) of a polyethylene glycol having an average number molecular weight of 400 is heated in a container fitted with a stirrer and an efficient reflux condenser to a temperature of 70° C. with agitation. Five hundred and seventy-five parts (5.25 moles) of propenoyl chloride is slowly added over two hours and carbon dioxide gas is simultaneously bubbled through the agitated mixture at a rate sufficient to remove the HCl gas as it forms. Agitation and the addition of carbon dioxide gas are continued for about one hour after all of the propenoyl chloride has been added to insure complete reaction with the polyethylene glycol.

EXAMPLE VIII

By the procedure described in Example V above, a polyurethane-polyethylene glycol diacrylate composition is prepared by reacting together:
Polyethylene glycol (m. wt. 1450): 666 parts
Diethylene glycol: 309 parts
Water: 3 parts
Polyethylene glycol diacrylate: 1630 parts
DESMODUR W ®: 1022 parts
Dimethyl ether of hydroquinone: 0.2 parts
Stannous octoate: 0.2 parts The polyethylene glycol diacrylate that is used in this Example is the product of Example VII prepared from polyethylene glycol having a molecular weight of 400 and propenoyl chloride.

EXAMPLE IX

A polyurethane-diethylene glycol diacrylate composition is manufactured "in situ" by the procedure described in Example V above by reacting together:
Polyethylene glycol (m. wt. 7500): 1644 parts
Diethylene glycol: 46 parts
Water: 10 parts
Diethylene glycol diacrylate: 500 parts
DESMODUR W ®: 300 parts
Dimethyl ether of hydroquinone: 0.05 parts
Dibutyl tin dilaurate: 0.2 parts The product may be extruded to form a hydrophilic catheter having desirable physical properties.

EXAMPLE X

A polyurethane-diethylene glycol diacrylate is manufactured "in situ" by reacting together:
Polyethylene glycol (m. wt. 1450): 1103 parts
Diethylene glycol: 18.1 parts
Rhodamine B: 4 parts
Diethylene glycol diacrylate: 500 parts
DESMODUR W ®: 716 parts
Stannous octoate: 2 parts
Dimethyl ether of hydroquinone: 0.1 part The diethylene and polyethylene glycols are melted together and the hydroquinone dissolved in the water and the Rhodamine B are added with stirring. Rhodamine B is a red dye obtained from Matheson, Coleman and Bell, Horwood, Ohio. The diethylene glycol diacrylate and stannous octoate are next added; the temperature adjusted to 60° C. and the DESMODUR W ® added in small increments to maintain the temperature below 80° C. This resin composition is dissolved in 95% ethanol to form a solution containing 10 percent solids and coated on a substrate. After the solvent has evaporated the polyurethane-diethylene glycol diacrylate film is exposed to ultraviolet light through a negative. A positive image useful in lithography is obtained.

In the solution of polyurethane-diethylene glycol diacrylate resin in ethanol described above in this Example, may be suspended 3 percent by weight (based on resin solids) of mercurous acetate. This solution can be applied to the hull of a boat and will be cured by the actinic rays of the sun to form an insoluble coating which will decrease drag resistance and inhibit marine growth by the slow release of mercury.

EXAMPLE XI

Polyethylene glycol having a molecular weight of 1450 (2468.6 parts) is melted and mixed at 60° C. with 324.2 parts of diethylene glycol and 12.3 parts of water. Delta gluconolactone (108.5 parts) and 1626.5 parts of DESMODUR W ® are then dispersed well and added to the mixture of polyols. The reaction mixture is cooled to 50° C. and 5 parts of dibutyl tin dilaurate is added with stirring. When the temperature of the reaction mixture reaches 80° C., it is poured into Teflon pans and cured in an oven at 100° C. for 20 minutes. The polymer is removed from the Teflon pans, cut into small cubes about 1 cm square, placed in a container with sufficient methanol to cover the resin and permitted to swell for 1 hour. Eight hundred and thirty parts by volume of a 10 percent by weight sodium hydroxide solution is added to the swollen polyurethane cubes and methanol and the mixture is stirred until the polyurethane cubes dissolve. The solution is then adjusted to pH 8.8 with hydrochloric acid. The solution is then filtered and the solids content is determined. To that amount of the solution which contains 200 parts of solids is added 133 parts (40 weight percent) of the product of Example VII prepared from polyethylene glycol having a molecular weight of 400 and propenoyl chloride and 0.27 parts of tertiary-butyl-perbenzoate catalyst. The solution may be cast as a film and cured in an oven at 135° C. to provide a solvent insoluble cross-linked hydrophilic film.

Alternatively, the methanol may be removed from the solution under vacuum at room temperature to provide a white solid that may be extruded to form water and gas permeable tubing useful in kidney dialysis equipment after soluble components, present in the resin have been leached out.

EXAMPLE XII

A polyurethane resin containing polypropylene oxide is prepared by the method described in Example II above by melting together:
Polypropylene glycol (m. wt. 2000): 300 parts
Diethylene glycol: 50 parts DESMODUR W ®: 225 parts and adding 3 parts by volume of stannous octoate. This polyurethane resin is 36% modified by the addition to the polyurethane solution in ethanol of 337.5 parts of diethylene glycol diacrylate and 0.65 parts of tertiary-butylperbenzoate as described in Example II. The cured polyurethane-diethylene glycol diacrylate polymer is similar in molecular weight and physical properties to the product of Example II but is more rigid (being 36% modified) and less hydrophilic (containing polypropylene oxide).

EXAMPLE XIII

A diacrylic acid ester of a polyethylene glycol having a number average molecular weight of 1450 is prepared by the method described in Example VII above by reacting 1450 parts (1 mole) of the polyethylene glycol with 230 parts (2.2 moles) of 2-methyl propenoyl chloride. This polyethylene glycol dimethacrylic acid ester may be added to any of the polyurethane resins described in the preceding Examples in amounts of 20% to 45% by the procedures described in Example II (dissolved in a solvent) and in Example V (in situ).

EXAMPLE XIV

To 4000 parts of the polyurethane solution in 95% ethanol described in Example I above is added with stirring 100 parts of diethylene glycol diacrylate and 0.208 parts of isopropyl percarbonate. The solution is cast onto a release surface and the solvent allowed to evaporate. The material will cure at ambient temperature to form a solvent insoluble hydrophilic membrane.

We claim:

1. An implant comprising a hydrophilic polyurethane diacrylate composition which will form a hydrogel upon immersion in water and is permeable to gases, ions and other low molecular weight species, which composition is dimensionally stable and exhibits memory, said polyurethane diacrylate composition comprising from about 90 to about 65 weight percent of a hydrophilic polyurethane resin characterized by terminal hydroxyl groups and from about 10 to about 35 weight percent of a diacrylate, said implant containing a medicament.

2. The implant of claim 1 wherein said medicament is an antitubercular drug.

3. The implant of claim 1 wherein said medicament is a drug protagonist.

4. The implant of claim 1 wherein said medicament is a hormone.

5. The implant of claim 1 wherein said medicament is a steroid.

6. The implant of claim 1 wherein said medicament is a vitamin.

7. The implant of claim 1 in the form of an intrauterine device.

8. The intrauterine device of claim 7 in the shape of a diaphragm.

9. The intrauterine device of claim 7 having distributed throughout said polyurethane diacrylate composition a contraceptive.

10. The intrauterine device of claim 9 wherein said contraceptive is lactic acid.

11. An implant comprising a hydrophilic polyurethane diacrylate composition which will form a hydrogel upon immersion in water; is permeable to gases, ions and other low molecular weight species; is dimensionally stable and exhibits memory; obtained by the reaction of from about 10 to about 35 weight percent of a diacrylate having the formula:

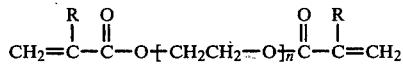

wherein R is selected from the group consisting of hydrogen and the methyl radical and n is a small whole number, such that the average molecular weight of the diacrylate is no greater than 1586; in the presence of from about 90 to about 65 weight percent of a hydrophilic polyurethane resin, said implant containing a medicament.

12. The implant of claim 11 wherein said medicament is an antitubercular drug.

13. The implant of claim 11 wherein said medicament is a drug protagonist.

14. The implant of claim 11 wherein said medicament is a hormone.

15. The implant of claim 11 wherein said medicament is a steroid.

16. The implant of claim 11 wherein said medicament is a vitamin.

17. The implant of claim 11 in the form of an intrauterine device.

18. The intrauterine device of claim 17 in the shape of a diaphragm.

19. The intrauterine device of claim 17 having distributed throughout said polyurethane diacrylate composition a contraceptive.

* * * * *